United States Patent [19]

Poli et al.

[11] Patent Number: 5,254,579
[45] Date of Patent: Oct. 19, 1993

[54] N-(5-THIOXO-L-PROLYL)-L-CYSTEINE, DERIVATIVES THEREOF, PROCESSES FOR THE PREPARATION THEREOF AND PHARMACEUTICAL COMPOSITIONS CONTAINING THEM

[75] Inventors: Stefano Poli; Germano Coppi; Giovanni Signorelli, all of Quinto de'Stampi-Rozzano, Italy

[73] Assignee: Poli Industria Chimica S.p.A., Milan, Italy

[21] Appl. No.: 879,907

[22] Filed: May 8, 1992

[30] Foreign Application Priority Data

May 29, 1991 [IT] Italy .................. MI91 A 001470

[51] Int. Cl.$^5$ .................. A61K 31/40; C07D 207/12; C07D 409/12; C07D 403/12
[52] U.S. Cl. .................. 514/422; 514/423; 548/527; 548/537; 548/519
[58] Field of Search .................. 548/537, 527; 514/423, 514/422

[56] References Cited

PUBLICATIONS

Inoue, et al., C.A. 91, (1979), 91:21136t.
Bjoerkman, et al., C.A., 94, (1981), 94:175517s.
Mueller, et al., C.A., 105, (1980), 105:79367t.
Benanti, et al., C.A., 112, (1990), 112:112100v.

Primary Examiner—Joseph Paul Brust
Attorney, Agent, or Firm—Griffin Butler Whisenhunt & Kurtossy

[57] ABSTRACT

N-(5-thioxo-L-prolyl)-L-cysteine and derivatives thereof, having interesting mucolytic-expectorant, antioxidant (radical-scavenger), antielastase, antiemphysema, immunostimulating and hepatoprotective activities and a low toxicity are described, as well as processes for the preparation thereof and pharmaceutical formulations for the use in therapy.

15 Claims, No Drawings

N-(5-THIOXO-L-PROLYL)-L-CYSTEINE, DERIVATIVES THEREOF, PROCESSES FOR THE PREPARATION THEREOF AND PHARMACEUTICAL COMPOSITIONS CONTAINING THEM

The present invention relates to compounds of general formula I

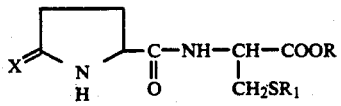

in which
X=O or S;
R is H, straight or branched $C_1$-$C_6$ alkyl, $C_6$-$C_{10}$ aryl, ($C_6$-$C_{10}$)aryl($C_1$-$C_6$)alkyl and ($C_1$-$C_4$)dialkylamino($C_1$-$C_{10}$)alkyl;
$R_1$ is H, straight or branched $C_1$-$C_6$ alkyl, ($C_1$-$C_6$)alkoxycarbonyl($C_1$-$C_8$)alkyl, $C_6$-$C_{10}$ aroyl, ($C_6$-$C_{10}$)aryl($C_1$-$C_6$)alkanoyl, $C_5$-$C_{11}$ heterocyclocarbonyl having one or more heteroatoms such as S, N, O; moreover
$R_1$ can represent S linked to an equal residue of formula (I), to give a disulfide;
with the proviso that, when X=O, R and $R_1$ cannot be at the same time H.

In compounds of formula (I), when X is O, R is preferably methyl, ethyl, benzyl, diethylaminoethyl and $R_1$ is preferably methyl, methoxycarbonylmethyl, 2-thenoyl and 3-thenoyl. On the contrary, when X is S, R and $R_1$, besides the preferred meanings reported above, can also be hydrogen.

Particularly preferred is the compound in which X=S, R and $R_1$ are at the same time H.

The invention also relates to the single enantiomers and diastereoisomers and mixtures thereof.

When R is hydrogen, the invention also comprises the salts of compounds of formula (I) with pharmaceutically acceptable bases.

The compound of formula (I) wherein X=O, R and $R_1$ are at the same time H, i.e. N-(5-oxo-L-prolyl)-L-cysteine, the preparation of which is described in literature (Inoue, Chozo; Yamada, Tsuyoshi—Jpn. Kokai Tokyo Koho 79 - 19, 966), is known to have anticataractogenic activity (Benanti, G.; Rizza, V.; EP-A-332,946); on the contrary, the pharmacological properties of compounds of formula (I), i.e. the mucolytic-expectorant, antioxidant (radical-scavenger), antielastase, antiemphysema, immunostimulating, hepatoprotecting activities were not previously known. Therefore, the present invention also relates to the use of N-(5-oxo-L-prolyl)-L-cysteine for the preparation of a medicament useful for the treatment of diseases of the respiratory system or as hepatoprotecting agent.

The compounds of the invention can be prepared according to the conventional schemes generally used for the peptide synthesis and for the synthesis of esters, thioesters or amides. From a general point of view, the preparation of the compounds of formula (I) comprises the reaction of a compound of formula (II):

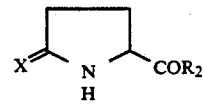

wherein X is as defined above and $R_2$ is hydroxy, halogen, $C_1$-$C_3$ alkoxy,
with a compound of formula (III)

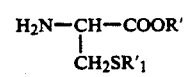

wherein R', $R'_1$ can have the above defined meanings except hydrogen; and possible hydrolysis reactions of the ester groups to give the compounds of formula (I) wherein R=H; reduction reactions of the disulfide group to give the compounds of formula (I) wherein $R_1$=H; alkylation and acylation reactions of the —SH group; transformation of X=O into X=S by means of thionating reagents.

Particularly, 5-oxo-L-proline or the reactive derivatives thereof (acid chloride, anhydride, imidazolide) are reacted with L-cystine dimethyl ester in anhydrous solvents and in the presence of acid-binding agents, such as suitable organic or inorganic bases, when the acid chloride is used. Alternatively, condensing agents such as dicyclohexylcarbodiimide or reactive esters in aprotic solvents such as dimethylformamide, acetonitrile, tetrahydrofuran and the like can be used. N,N'bis(5-oxo-L-prolyl)-L-cystine dimethyl ester is reduced with zinc in aqueous acetic acid to N-(5-oxo-L-prolyl)-L-cysteine methyl ester.

N-(5-oxo-L-prolyl)-L-cysteine methyl ester is alkylated or acylated at the sulfhydryl group, then it is transformed into the 5-thioxo analogues of general formula I with X=S and R and $R_1$ different from H, by thionation with the Lawesson's reagent according to procedures already known in literature (Torben P. Andersen et al., Liebigs Ann. Chem. 1986, 269-279).

Thionation of N-(5-oxo-L-prolyl)-L-cysteine methyl ester with the Lawesson's reagent and the subsequent alkali hydrolysis with two sodium hydroxide equivalents in aqueous solution yields N-(5-thioxo-L-prolyl)-L-cysteine.

Alternatively, the 5-oxo-L-proline and 5-thioxo-L-proline reactive esters can be reacted with S-ethylcarbamoyl-L-cysteine (S. Guttmann, Helv. Chim. Acta, 1966, (49), 83-95) or the alkyl esters thereof in aprotic solvents, such as dimethylformamide, acetonitrile, tetrahydrofuran and the like, and the obtained products can be deprotected at the sulfur atom by conventional methods (1N sodium hydroxide or 1N sodium methoxide in methanol) to give N-(5-oxo(or 5-thioxo)-L-prolyl)-L-cysteine (I: X=O or S, R—$R_1$=H).

Compounds of formula I have interesting pharmacological properties; particularly they have marked mucolytic-expectorant, antioxidant (radical-scavenger), antielastase, antiemphysema, immunostimulating, hepatoprotecting activities together with a very low toxicity.

More precisely, in the test of elimination of phenol red from the respiratory fluid (G. Coppi and M. T. Gatti, Il Farmaco Ed. Prat. 4, 541, 1989), the compounds show, compared with controls, increases in dye secretion higher than those of N-acetyl-L-cysteine.
(Table N. 1).

TABLE N. 1

Mucosecretolytic activity (phenol red test in the mouse)

| Compound | Dose (mg/kg/os) | Mice N. | Mean secretion (total µg) (mean ± S.E.) | Variat. (%) |
|---|---|---|---|---|
| Controls | — | 10 | 2.73 ± 0.18 | — |
| Ic | 100 | 5 | 6.64 ± 1.00** | +143.2 |
| Id | 100 | 5 | 5.39 ± 0.59** | +97.4 |
| Ie | 100 | 5 | 5.81 ± 0.62** | +112.8 |
| N-(5-oxo-L-prolyl)-L-cysteine | 100 | 5 | 5.26 ± 0.25** | +92.7 |
| N-acetyl-L-cysteine | 100 | 5 | 4.42 ± 0.83** | +61.9 |

**p <0.01 Dunnett's "t" test

The antioxidant (radical-scavenger) activity was studied by means of the DPPH in vitro test and with the paracetamol in vivo test. The activity with DPPH (α,α-diphenyl-β-picrylhydrazyl) was tested using various concentrations of the test compounds (K. Kato et al. J. Med. Chem. 31, 793, 1988).

The compounds of the invention evidence an antioxidant activity analogous to the one of well-known control compounds (Table N.2).

TABLE n. 2

In vitro antioxidant activity (DPPH test)

| Compound | Variat. (%) of absorbancies at concentrations of | | |
|---|---|---|---|
| | $10^{-4}M$ | $5.10^{-5}M$ | $10^{-5}M$ |
| Ic | −82.7 | −49.1 | −10.4 |
| Id | −79.1 | −51.8 | −14.3 |
| Ie | −83.1 | −51.8 | −14.3 |
| N-(5-oxo-L-prolyl)-L-cysteine | −88.1 | −49.6 | −29.6 |
| N-acetyl-L-cysteine | −86.3 | −47.9 | −10.4 |
| L-cysteine | −83.7 | −56.5 | −10.9 |
| L-ascorbic acid | −86.0 | −49.5 | −17.6 |

The in vivo antioxidant (radical scavenger) activity was evidenced by means of the protection test against paracetamol acute toxicity. Male Crl: CD-1 (ICR) BR mice, weighing 25-30 g, were treated intraperitoneally with 1000 mg/kg (1 ml/kg) of paracetamol dissolved in 20% DMF in water immediately before the administration. The compounds were orally administered 30 minutes before and 5 hours after paracetamol; mortality was observed in the 6 subsequent days.

The compounds of the invention have an antioxidant activity analogous to or higher than that of N-acetyl-L-cysteine (Table n. 3).

TABLE N. 3

In vivo antioxidant activity (paracetamol test)

| Compound | Dose (mg/kg/os) | Mice N. | Mortality (%) | Variat. vs controls (%) |
|---|---|---|---|---|
| Controls | — | 10 | 90 | — |
| Ic | 100 | 10 | 50 | 45.4 |
| Id | 100 | 10 | 50 | 45.4 |
| Ie | 100 | 10 | 30 | 66.7 |
| N-(5-oxo-L-prolyl)-N-cysteine | 100 | 10 | 30 | 66.7 |
| N-acetyl-L-cysteine | 100 | 10 | 50 | 45.4 |

The compounds of present invention have antielastase activity on porcine pancreatic elastase (M. Luisetti et al. Bioch. Bioph. Res. Commun. 165, 568, 1989) at concentrations from $10^{-4}$ to $10^{-5}M$; inhibitions for the various compounds varying from 30% to 70%.

The compounds of present invention also have an interesting antiemphysema activity in the hamster (P. J. Stone et al., Amer. Rev. Respir. Dis., 124, 56, 1981). Pancreatic elastase-induced emphysema was morphometrically measured by evaluating in µm the mean linear intercept (M.L.I.) (J. Kleinerman et al., Amer. Rev. Respir. Dis., 121, 381, 1980). The compounds reduce the M.L.I. increase in elastase-induced emphysema in percentages from 32.3 to 43.6% and in a statistically significant way after 4 week treatment at doses of 0.25 mM/kg os.

The compounds of formula I have an immunostimulating activity which was measured by evaluating the superoxide anion production in macrophages of prednisolone-immunodepressed mice (N. P. Cumming, M. J. Pabst, I. Exp. Med., 152, 1659, 1980). Treatment with prednisolone induced an immunodepression which is evidenced by a lower production of superoxide anion; the concomitant treatment with the compounds of the invention stimulates macrophages to produce $O_2$ up to values similar to those of non-immunodepressed animals.

The hepatoprotective activity was evaluated by means of the $CCl_4$ intoxication test in the rat (And.C. Ferreyra et al., Toxic. Appl. Pharmacol., 27, 558, 1974). The compounds of formula I reduce serum GPT and GOT in a significantly higher way than N-acetylcysteine, both compounds being administered at doses of 0.25 mM/kg i.p.

The compounds of present invention have a very low acute toxicity; all of the $LD_{50}$s by the oral route in the rat being >2.000 mg/kg.

The compounds of the invention, as well as the pharmaceutically acceptable salts thereof, due to the pharmacological properties and low toxicity thereof, can be used as active ingredients for the preparation of medicaments useful for the treatment of diseases of the respiratory system and as hepatoprotecting agents.

A further object of present invention is provided by pharmaceutical compositions containing, as the active ingredients, the compounds of formula I (or the enantiomers and/or diastereoisomers and/or mixtures thereof) or the pharmaceutically acceptable salts thereof, for the aerosol, parenteral, oral and rectal administrations in form of vials, oral suspensions, capsules, tablets, sachets and suppositories.

Examples of pharmaceutical formulations according to the invention are:

vials containing 25 to 250 mg of active ingredient, syrup containing 50 to 500 mg of active ingredient for dose, hard-gelatin capsules or Scherer capsules containing 50 to 500 mg of the active ingredient, sachets containing 50 to 500 mg of active ingredient in suitable excipients, suppositories containing 100 to 1000 mg of active ingredient in a suitable carrier for the nepiological and pediatric uses and for adults.

The daily dose varies from 50 to 2000 mg of active ingredient in the treatment of diseases of the respiratory system (particularly emphysema, asthma, chronic bronchitis, tracheobronchitis and the like) and hepatic diseases (acute, infective and chronic hepatitis, hepatic steatosis, and the like).

The following examples illustrate the preparation of some compounds of formula (I).

EXAMPLE 1

N,N'-bis-(5-oxo-L-prolyl)-L-cystine dimethyl ester (Ia)

56 ml (0.4 m) of triethylamine are dropped into a solution of 68.2 g (0.2 m) of L-cystine dimethyl ester 2HCl in 200 ml of dimethylformamide, under stirring at 0° C. The reaction mixture is stirred for 10 minutes, then triethylamine hydrochloride is filtered off, washing with some chilled dimethylformamide. The resulting solution is slowly added with a solution of 51.6 g (0.4 m) of 5-oxo-L-proline in 200 ml of dimethylformamide at 0° C. and under stirring. Finally 82.4 g (0.4 m) of dicyclohexylcarbodiimide are added and stirring is continued for one hour at 0° C. After that, the mixture is left to warm to room temperature and, after 16 hours, dicyclohexylurea is filtered off, washing with chilled dimethylformamide. The solution is evaporated under vacuum at 40° C./0.1 mm until dimethylformamide is completely removed, and the oily residue is warm dissolved in 250 ml of methanol. Upon cooling to 0° C., the product crystallizes and it is filtered and washed with chilled methanol. After drying at 50° C. under vacuum, 83 g (84.7%) of the product are obtained, m.p. 160°-162° C.

E.A. for $C_{18}H_{26}N_4O_8S_2$ (490.56)

Calc. %: C: 44.07; H: 5.34; N: 11.42; S: 13.07
Found %: C: 44.66; H: 5.44; N: 11.61; S: 13.17
$[\alpha]_D^{22} = -157.66°$ (c=1% in $H_2O$)

$^1H$ NMR (200 MHz, $D_2O$, δ=ppm from TMS): 2.00-2.20 and 2.30-2.60 (m, 4H, $CH_2$—$CH_2$); 3.00 and 3.30 (ABX syst.: AB portion, 2H, $CH_2S$—; J=8.5; 5.8; 14.5 Hz); 3.72 (s, 3H, $OCH_3$); 4.35 (dd, 1H, C$\underline{H}$—CO—NH; J=8.7; 4.8 Hz); 4.80 (ABX syst.: X portion, 1H, C$\underline{H}$—$COOCH_3$).

$^{13}C$ NMR (50 MHz, $D_2O$, δ=ppm from TMS): 28.0 and 32.0 ($CH_2$—$CH_2$); 41.0 (—$CH_2S$—); 54.5 (—$\underline{C}H$—$COOCH_3$); 56.0 ($OCH_3$); 59.6 (—$\underline{C}H$—); 174.5 ($\underline{C}OOCH_3$); 178.0 (CH—$\underline{C}O$—NH); 185.0 ($\underline{C}H_2\underline{C}O$—NH).

EXAMPLE 2

N,N'-bis(5-oxo-L-prolyl)-L-cystine (Ib)

33 ml of 1N sodium hydroxide are slowly added to a solution of 7.35 g (0.015 m) of compound Ia in 45 ml of $H_2O$, at 20° C. The reaction mixture is stirred for 30 minutes, then 40 ml of Amberlite IR 120 (H+) freshly regenerated resin are added thereto and stirring is continued for 30 more minutes. The resin is filtered, washing thoroughly with water. The aqueous solution is evaporated under vacuum at 40° C. to constant weight of the residue, which is then taken up into 50 ml of methanol, heating until complete dissolution. The solution is left to stand for some hour at 0° C., to obtain a crystal which is filtered and dried at 50° C. under vacuum, to obtain 4,2 g (60.6%) of product, m.p. 191°-193° C.

E.A. for $C_{16}H_{22}N_4O_8S_2$ (462.51)

Calc. %: C: 41.55; H: 4.79; N: 12.11; S: 13.86
Found %: C: 41.78; H: 4.86; N: 12.15; S: 13.80
$[\alpha]_D^{22} = -65.5°$ (c=1% in $H_2O$)

$^1H$ NMR (200 MHz, DMSO-d6, δ=ppm from TMS): 1.84-2.49 (two m, respectively 1H and 3H, $CH_2$—$CH_2$); 2.91-3.23 (eight lines 2H, $CH_2$—S; J=14.0; 10.0; 5.5 Hz); 4.05 (dd, 1H, CH—CO—NH; J=8.0; 4.0 Hz); 4.46-4.57 (eight lines, 1H, CH—COOH); 7.84 (s, 1H, NH exch.); 8.43 (d, 1H, NH, J=8.0 Hz); 13.0-13.10 (br. s, 1H, COOH).

$^{13}C$ NMR (50 MHz, $D_2O$, δ=ppm from TMS): 28.21 ($CH_2$—$CH_2$—CH); 32.18 (CO—$CH_2$); 41.31 ($CH_2S$); 54.65 ($\underline{C}H$—COOH); 59.87 ($\underline{C}H$—CO); 176.35 (—$\underline{C}OOH$); 177.97 (CH—$\underline{C}O$—NH); 185.23 ($CH_2$—$\underline{C}O$—NH).

EXAMPLE 3

N-(5-oxo-L-prolyl)-L-cysteine methyl ester (Ic)

A solution of 9.8 g (0.02 m) of compound Ia in 100 ml of acetic acid/water 1:1 is heated to 50° C., then 2 g of zinc powder are added thereto, keeping this temperature for 90 minutes. The reaction mixture is cooled to room temperature and the zinc excess is filtered off. The filtered solution is evaporated under vacuum to dryness, the residue is dissolved in 100 ml of water and the solution is treated with 40 ml of freshly regenerated Amberlite IR 120 (H+) under stirring for 30 minutes. The resin is filtered off, thoroughly washing with $H_2O$. The aqueous solution is evaporated under vacuum of 0.1 mm on a 40° C. bath to constant weight of the solid residue. The residue is warm dissolved in the minimum amount of dimethoxyethane and the resulting solution is left to crystallize for some hour at 0° C., then it is filtered and dried to obtain 7.8 g (79.2%) of product, m.p. 114°-116° C.

E.A. for $C_9H_{14}N_2O_4S$ (246.27)

Calc. %: C: 44.21; H: 5.73; N: 11.37; S: 13.01
Found %: C: 44.11; H: 5.78; N: 11.33; S: 12.89
$[\alpha]_D^{22} = -26.87°$ (c=1% in $H_2O$)

$^1H$ NMR (200 MHz, $D_2O$, δ=ppm from TMS): 2.00-2.14 and 2.30-2.60 (m, 4H, $CH_2$—$CH_2$); 2.95 (ABX syst.: AB portion, 2H, $CH_2SH$; J=13.5; 7.0; 5.0 Hz); 3.70 (s, 3H, $OCH_3$); 4.35 (dd, 1H, C$\underline{H}$—CO—NH; J=8.9; 5.3 Hz); 4.64 (ABX syst.: X portion, 1H, C$\underline{H}$—$COOCH_3$).

$^{13}C$ NMR (50 MHz, $D_2O$, δ=ppm from TMS) 27.6 and 28.0 ($CH_2$—$CH_2$); 32.0 ($CH_2SH$); 56.0 (—$\underline{C}H$—$COOCH_3$); 58.0 (—$OCH_3$); 60.0 (—$\underline{C}H$—); 174.5 (—$\underline{C}OOCH_3$); 178.0 (—CH—$\underline{C}O$—NH); 185.0 ($CH_2$—$\underline{C}O$—NH).

EXAMPLE 4

N-(5-thioxo-L-prolyl)-L-cysteine methyl ester (Id)

A suspension of 24.6 g (0.1 m) of compound Ic in 300 ml of dimethoxyethane is added with 20.2 g (0.05 m) of Lawesson's reagent and it is stirred at room temperature for 3 hours. Dimethoxyethane is evaporated off under vacuum at low temperature (max. 30° C.) to obtain a pitchy residue which is warm dissolved in 100 ml of methanol. Upon cooling to 0° C., a first amount of 12.6 g of product crystallizes, still containing traces of decomposition products of the Lawesson's reagent. Crystallization mother liquors are evaporated under vacuum to half the starting volume and left to crystallize for a night at 0° C., to obtain a second amount of 3.6 g of product, which is slightly less pure than the first one. The two amounts are combined (16.2 g) and recrystallized from 200 ml of $H_2O$.

Upon cooling to 5° C., filtration and drying at 40° C. under vacuum, 12.85 g (49%) of product are obtained, m.p. 177°-178° C.

E.A.. for $C_9H_{14}N_2O_3S_2$ (262.33)

Calc. %: C: 41.22; H: 5.38; N: 10.67; S: 24.44
Found %: C: 41.05; H: 5.38; N: 10.59; S: 24.22
$[\alpha]_D^{22} = -12.33°$ (c=0.86% in methanol)

$^1H$ NMR (200 MHz, DMSO-d6, δ=ppm from TMS): 1.90-2.10 and 2.30-2.50 (2m, 4H, $CH_2$—$CH_2$); 2.65 (t, 1H, SH); 2.85 (m, 2H, CH$_2$SH); 3.70 (s, 3H, OCH$_3$); 4.40–4.60 (m, 2H, CH—CO and CH—COOCH$_3$); 8.65 (d, 1H, CO—NH exch.); 10.30 (s, 1H, CS—NH exch.).

$^{13}$C NMR (50 MHz, DMSO-d6, δ=ppm from TMS): 25.6 and 28.2 (CH$_2$—CH$_2$); 43.0 (CH$_2$—SH); 52.5 (CH—COOCH$_3$); 55.0 (OCH$_3$); 63.2 (CH—CO); 170.6 (COOH$_3$); 171.0 (CH—CO); 205.5 (C=S).

EXAMPLE 5

N-(5-thioxo-L-prolyl)-L-cysteine (Ie)

6.55 g (0.025 m) of compound Id are dissolved in 50 ml of 1N sodium hydroxide and the mixture is left for 24 hours at room temperature in a sealed container, under nitrogen. The solution is neutralized with an equivalent amount of 37% hydrochloric acid (4.2 ml), then it is cooled to 0° C. to crystallize a first amount (4.75 g) of product. By concentration under vacuum of mother liquors to one third of the starting volume, after a night at 0° C., a second amount of product (0.7 g) is obtained, which is qualitatively equal to the first one. The two amounts are combined (5.45 g) and recrystallized from 25 ml of ethanol. After cooling at 0° C. for some hours, the mixture is filtered and dried at 60° C./0.1 mm to obtain 4.6 g (74.2%) of product, m.p. 147°–148° C.

E.A.. for C$_8$H$_{12}$N$_2$O$_3$S$_2$ (248.31)

Calc. %: C: 38.69; H: 4.87; N: 11.28; S: 25.82
Found %: C. 38.61; H: 4.85; N: 11.25; S: 25.88
[α]$_D^{22}$ = +14.13° (c=0.98% in methanol)

$^1$H NMR (200 MHz, DMSO-d6, δ-ppm from TMS): 1.90–2.40 (m, 4H, CH$_2$—CH$_2$); 2.60–3.60 (m, 3H, CH$_2$—SH); 4.35–4.60 (m, 2H, CH—CO and CH—COOH); 8.50 (d, 1H, CO—NH, J=8 Hz); 10.30 (s, 1H, CS—NH); 12.40–13.40 (br. s, 1H, COOH).

$^{13}$C NMR (50 MHz, DMSO-d6, δ=ppm from TMS): 26.0 and 28.0 (CH$_2$—CH$_2$); 43.0 (CH$_2$SH); 54.5 (CH—COOH); 63.5 (CH); 171.0 and 172.0 (COOH and CO—N); 205.0 (C=S).

EXAMPLE 6

N-(5-oxo-L-prolyl)-L-S-methyl-cysteine methyl ester (If)

A solution of 0.46 g of metal sodium in 15 ml of methanol is slowly added to a suspension of 4.92 g (0.02 m) of compound Ic in 40 ml of methanol, at 5°–10° C. The reaction mixture is stirred until complete dissolution of the product. Temperature is lowered to −10° C. and a solution of 2.42 g (0.02 m) of methyl iodide in 15 ml of methanol is added very slowly. Stirring is continued for 30 minutes, then methanol is evaporated off under vacuum. The oily is dissolved in 40 ml of H$_2$O and the aqueous solution is repeatedly extracted with methylene chloride. The combined organic extracts are dried over sodium sulfate, then methylene chloride is evaporated off to constant weight of the oily residue, which is dissolved in 20 ml of acetone and the solution is diluted with ethyl ether to crystalize. After some hour standing at low temperature, crystals are filtered, dried at 40° C. under vacuum, to obtain 3.91 g (75.3%) of product, m.p. 83°–85° C. E.A.. for C$_{10}$H$_{16}$N$_2$O$_4$S (260.31)

Calc. %: C: 46.14; H: 6.20; N: 10.76; S: 12.31
Found %: C: 46.03; H: 6.18; N: 10.77; S: 12.31
[α]$_D^{22}$ = −58.2° (c=1% in H$_2$O)

$^1$H NMR (200 MHz, DMSO-d6, δ=ppm from TMS): 1.84–2.36 (two m, respectively 1H and 3H, CH$_2$CH$_2$); 2.08 (s, 3H, SCH$_3$); 2.73–2.95 (eight lines, 2H, CH$_2$S, J=14.0; 10.0; 5.0 Hz); 3.67 (s, 3H, OCH$_3$); 4.08 (dd, 1H, CH—CO—NH, J=8.0; 4.0 Hz); 4.45–4.56 (eight lines, 1H, CH—COOCH$_3$); 7.87 (s, 1H, NH exch.); 8.50 (d, 1H, NH, J=8.0 Hz).

$^{13}$C NMR (50 MHz, D$_2$O, δ=ppm from TMS): 18.0 (SCH$_3$); 28.0 (CH$_2$—CH$_2$—CH); 32.0 (CO—CH$_2$); 37.6 (CH$_2$S); 55.0 (CH—COOCH$_3$); 56.0 (OCH$_3$); 60.0 (CHCO); 175.4 (COOCH$_3$); 178.0 (CH—CO—NH); 185.0 (CH$_2$—CO—NH).

EXAMPLE 7

N-(5-thioxo-L-prolyl)-L-S-methyl-cysteine methyl ester (Ig)

3.9 g (0.015 m) of compound If are dissolved in 50 ml of dimethoxyethane, 3.03 g (0.0075 m) of Lawesson's reagent are added and the reaction mixture is stirred for 3 hours. Dimethoxyethane is completely evaporated off and the solid residue is crystallized from the minimum amount of ethanol. The ethanol solution is cooled, filtered and dried to obtain 3.31 g (80%) of product, m.p. 163°–164° C.

E.A.. for C$_{10}$H$_{16}$N$_2$O$_3$S$_2$ (276.37)

Calc. %: C: 43.45; H: 5.83; N: 10.13; S: 23.20
Found %: C: 43.29; H: 5.81; N: 10.09; S: 23.20
[α]$_D^{20}$ = −46.8° (c=1% in methanol)

$^1$H NMR (200 MHz, DMSO-d6, δ=ppm from TMS): 1.90–2.95 (three m, respectively 1H, 1H and 4H, CH$_2$—CH$_2$ and CH$_2$S); 2.09 (s, 3H, S—CH$_3$); 3.67 (s, 3H, OCH$_3$); 4.42–4.55 (m, 2H, CH—CO and CH—COOCH$_3$); 8.67 (d, 1H, CO—NH exch., J=8.0 Hz); 10.31 (s, 1H, CS—NH exch.).

$^{13}$C NMR (50 MHz, CDCl$_3$, δ=ppm from TMS): 16.44 (SCH$_3$); 28.85 (CH$_2$—CH$_2$—CH); 36.83 (CS—CH$_2$); 43.15 (CH$_2$S); 51.85 (CH—COOCH$_3$); 54.46 (OCH$_3$); 64.66 (CH—CO); 171.02 (COOCH$_3$); 171.75 (CH—CO—NH); 208.52 (C=S).

EXAMPLE 8

N-(5-thioxo-L-prolyl)-L-S-methyl-cysteine (Ih)

5.52 g (0.02 m) of compound Ig are dissolved in 40 ml of 1N sodium hydroxide and left at room temperature for one hour. The reaction solution is diluted with H$_2$O and treated for 30 minutes under stirring with 50 ml of freshly regenerated Amberlite IR 120 (H$^+$). The resin is filtered off, washing with water. The aqueous solution is concentrated under vacuum to small volume, cooled for some hours at 0° C. and the product is crystallized, filtered and dried, to obtain 3.98 g (76%) of product, m.p. 158°–160° C.

For C$_9$H$_{14}$N$_2$O$_3$S$_2$ (262.33)

Calc. %: C: 41.20; H: 5.38; N: 10.68; S: 24.44
Found %: C: 40.98; H: 5.34; N: 10.70; S: 24.50
[α]$_D^{20}$ = −35.9° (c=1% in H$_2$O)

$^1$H NMR (200 MHz, DMSO-d6, δ=ppm from TMS): 1.91–2.95 (three m, respectively 1H, 1H and 4H, CH$_2$—CH$_2$ and CH$_2$S); 2.10 (s, 3H, SCH$_3$); 4.37–4.48 (m, 2H, CH—CO and CH—COOH); 8.50 (d, 1H, CO—NH exch., J=8.0 Hz); 10.31 (s, 1H, CS—NH exch.).

$^{13}$C NMR (50 MHz, DMSO-d6, δ=ppm from TMS): 15.63 (SCH$_3$); 27.80 (CH$_2$—CH$_2$—CH); 35.20 (CS—CH$_2$); 43.09 (CH$_2$—S); 52.12 (CH—COOH); 63.25 (CH—CO); 170.92 (—COOH); 172.07 (CO—NH); 205.51 (C=S).

EXAMPLE 9

N-(5-oxo-L-prolyl)-L-S-(2-thenoyl)-cysteine methyl ester (Ii)

1.4 ml (0.01 m) of triethylamine are added to a solution of 2.46 g (0.01 m) of compound Ic in 20 ml of dimethylformamide and the mixture is cooled to 0° C., then it is slowly added with a solution of 1.51 g (0.01 m) of thiophene-2-carbonyl chloride in 10 ml of acetone.

Stirring is continued for 30 minutes, then triethylamine hydrochloride is filtered off, washing with acetone. The solution is evaporated under vacuum to completely remove dimethylformamide and the oily residue is taken up into water in which it quickly solidifies. The crude product is filtered and crystallized from a mixture of equal amounts of water and methanol, to obtain 3 g (84.2%) of product, m.p. 140°-142° C.

E.A.. for $C_{14}H_{16}N_2O_5S_2$ (356.42)

Calc. %: C: 47.17; H: 4.52; N: 7.85; S: 17.99
Found %: C: 47.06; H: 4.44; N: 7.79; S: 18.12
$[\alpha]_D^{20} = -14.9°$ (c=1% in $H_2O$)

$^1$H NMR (200 MHz, DMSO-d6, δ=ppm from TMS): 1.85-1.99 and 2.06-2.36 (3m, 4H, $CH_2$—$CH_2$); 3.28-3.84 (ABX syst.: AB portion, 2H, $CH_2S$, J=14.0; 8.0; 5.2 Hz); 3.68 (s, 3H, $OCH_3$); 4.05 (dd, 1H, C$\underline{H}$—CO—NH); 4.51-4.58 (ABX syst.: X portion, 1H, C$\underline{H}$—COOCH$_3$); 7.28 (dd, 1H, $H_4$ thiophene, J=4.8 Hz); 7.85 (s, 1H, NH prolyl, exch.); 7.92 (dd, 1H, $H_5$ thiophene, J=4.8; 1, 1 Hz); 8.09 (dd, 1H, $H_3$ thiophene); 8.61 (d, 1H, CO—NH exch., J=8.0 Hz).

$^{13}$C NMR (50 MHz, DMSO-d6, δ=ppm from TMS): 25.8 ($CH_2$—S); 29.2 and 30.0 ($CH_2$—$CH_2$); 51.8 ($\underline{CH}$—COOCH$_3$); 52.6 ($OCH_3$); 55.8 ($\underline{CH}$—CO—NH); 129 ($C_4$ thiophene); 132.5 ($C_5$ thiophene); 135.2 ($C_3$ thiophene); 140.5 ($C_2$ thiophene); 170.4; 173.0; 178.0 and 182.5 (four-CO groups).

We claim:

1. Compounds of general formula I

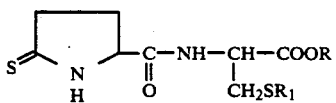

in which

R is H, straight or branched $C_1$-$C_6$ alkyl, phenyl, phenyl ($C_1$-$C_6$)alkyl and ($C_1$-$C_4$)dialkylamino($C_1$-$C_{10}$)alkyl;

$R_1$ is H, straight or branched $C_1$-$C_6$ alkyl, ($C_1$-$C_6$)alkoxycarbonyl($C_1$-$C_8$)alkyl, benzoyl, phenyl($C_1$-$C_6$)alkanoyl, 2-thenoyl and 3-thenoyl; $R_1$ can represent S linked to an equal residue of formula (I), to give a disulfide;

the enantiomers, diastereoisomers and mixtures thereof and the pharmaceutically acceptable salts thereof.

2. Compounds according to claim 1 in which R is selected from hydrogen, methyl, ethyl, benzyl, diethylaminoethyl.

3. Compounds according to claim 1 in which $R_1$ is selected from hydrogen, methyl, methoxycarbonylmethyl, 2-thenoyl and 3-thenoyl.

4. N-(5-thioxo-L-prolyl)-L-cysteine methyl ester.

5. N-(5-thioxo-L-prolyl)-L--cysteine.

6. Compounds of claim 1 as therapeutical agents in a pharmaceutically acceptable carrier.

7. Pharmaceutical compositions containing as the active ingredient the compounds of claim 1 at a dosage ranging from 25 to 1000 mg in admixture with pharmaceutically acceptable carriers.

8. A method for treating a mammal for a respiratory disease and in need of such treatment, comprising administering to the mammal a respiratory disease therapeutically effective amount of a compound of claim 1.

9. The method of claim 8 wherein the respiratory disease is one or more of emphysema, asthma, chronic bronchitis, pulmonary inflammation, tracheobronchitis and the therapeutically effective amount is at least an immunostimulating amount.

10. The method of claim 8 wherein the therapeutically effective amount is between 25 and 2000 mg.

11. A method for treating a mammal for a hepatic disease and in need of such treatment, comprising administering to the mammal a hepatic disease therapeutically effective amount of a compound of claim 1.

12. The method of claim 11 wherein the hepatic disease is one or more of hepatitis and hepatic steatosis.

13. The method of claim 12 wherein the hepatitis is acute, infective or chronic hepatitis.

14. The method of claim 11 wherein the therapeutically effective amount is at least an immunostimulating amount.

15. The method of claim 14 wherein the therapeutically effective amount is between 50 to 2000 mg.

* * * * *